(12) United States Patent
Drege et al.

(10) Patent No.: US 6,853,942 B2
(45) Date of Patent: Feb. 8, 2005

(54) METROLOGY HARDWARE ADAPTATION WITH UNIVERSAL LIBRARY

(75) Inventors: Emmanuel Drege, San Jose, CA (US); Junwei Bao, Santa Clara, CA (US); Srinivas Doddi, Fremont, CA (US); Vi Vuong, Fremont, CA (US)

(73) Assignee: Timbre Technologies, Inc., Santa Clara, CA (US)

( * ) Notice: Subject to any disclaimer, the term of this patent is extended or adjusted under 35 U.S.C. 154(b) by 156 days.

(21) Appl. No.: 10/213,485

(22) Filed: Aug. 6, 2002

(65) Prior Publication Data

US 2003/0187604 A1 Oct. 2, 2003

Related U.S. Application Data

(63) Continuation-in-part of application No. 10/108,818, filed on Mar. 26, 2002, now Pat. No. 6,721,691.

(51) Int. Cl.[7] .......................... G06F 19/00; G01B 11/24; G01B 9/02; G06K 9/46
(52) U.S. Cl. ...................... 702/119; 356/369; 356/499; 702/189; 438/16; 382/144
(58) Field of Search ............................. 702/28, 81, 117, 702/119, 123, 155, 179; 703/2; 355/77; 382/144; 256/237.2, 356, 355, 369, 384, 400, 401, 601, 354; 438/14, 16

(56) References Cited

U.S. PATENT DOCUMENTS

| | | | |
|---|---|---|---|
| 5,098,190 A | * 3/1992 | Wijntjes et al. | 356/499 |
| 5,164,790 A | 11/1992 | McNeil et al. | 356/496 |
| 5,655,110 A | 8/1997 | Krivokapic et al. | 716/19 |
| 6,449,031 B1 | 9/2002 | Grodnensky et al. | 355/77 |
| 6,458,610 B1 | 10/2002 | Lensing et al. | 438/16 |
| 2002/0018217 A1 | 2/2002 | Weber-Grabau et al. | 356/601 |
| 2002/0035455 A1 | * 3/2002 | Niu et al. | 703/4 |
| 2002/0113966 A1 | 8/2002 | Shchegrov et al. | 356/369 |
| 2003/0071996 A1 | * 4/2003 | Wang et al. | 356/369 |

* cited by examiner

*Primary Examiner*—John Barlow
*Assistant Examiner*—John Le
(74) *Attorney, Agent, or Firm*—Morrison & Foerster LLP

(57) ABSTRACT

To generate sets of coefficients for use in optical metrology of semiconductor structures, at least three optical metrology signals for a set of parameters are obtained. The optical metrology signals are indicative of light diffracted from a semiconductor structure, and a value of at least one parameter of the set of parameters is varied to produce each signal. Functional relationships between the at least three optical metrology signals are obtained, the functional relationships including at least three coefficient values. At least three sets of coefficients from the at least three coefficient values of the functional relationships are determined.

62 Claims, 12 Drawing Sheets

METROLOGY HARDWARE ADAPTATION WITH UNIVERSAL LIBRARY

CROSS-REFERENCE TO RELATED APPLICATIONS

This application is a continuation-in-part of U.S. patent application Ser. No. 10/108,818 now U.S. Pat. No. 6,721,691, entitled "Metrology Hardware Specification using Hardware Simulator," filed on Mar. 26, 2002, and is incorporated herein by reference in its entirety.

BACKGROUND

1. Field

The present application relates to metrology for semiconductor applications, and in particular to an optical metrology method and system for reducing measurement inaccuracies.

2. Description of Related Art

As integrated circuits (IC) evolve towards smaller geometries of the IC features and faster response times, new challenges are encountered in the manufacturing process. In particular, accurate measurements of the smaller feature sizes are becoming increasingly more difficult. Knowledge of the dimensions of gratings and/or periodic structures, however, is essential to determine if the dimensions of the IC features are within acceptable ranges and if, for example, a particular fabrication process causes sidewalls of the features to be tapered, vertical, T-topped, undercut, have footings, and the like, which can affect final device performance.

Optical metrology has emerged as an effective tool for measuring IC features of small sizes. Optical metrology uses optical signals that are typically non-destructive to the semiconductor materials and small features that are being measured. Further, optical metrology systems can be used for determination of thickness and topographic information, which include CD measurements, as well as optical properties (e.g., refractive index and extinction coefficient n&k) of semiconductor structures.

In one optical metrology system, scatterometry is used to reconstruct a diffraction grating profile from its optical diffraction responses at a fixed incident angle and multiple wavelengths. A library-based methodology for profile extraction is provided, where libraries comprising of simulated optical metrology signals are created for given grating profiles. Alternatively, the method can be carried out for a variety of control parameters beside wavelengths. For example, a fixed wavelength and multiple incident angles, or a hybrid of different angles and wavelengths can be used. An additional example of control parameters besides incident angle and wavelength is illumination polarization state, which can be used alone or in any combination with the two previous cited parameters.

The optical metrology hardware typically used in conjunction with such scatterometry measurements includes, for example, a light source, a detection scheme, and a complex assortment of optical and mechanical components. These various hardware pieces involve parameters that are, with respect to their design values, difficult to set equal from tool-to-tool. Furthermore, with time, and the effect of outside factors, for example, vibrations, pressure, humidity, part replacements, and the like, the parameters within a single tool can vary as well. In addition to the variability of metrology hardware-related parameters, material based parameters such as the optical characteristics n and k, may vary from sample batch to batch, i.e., in different semiconductor wafer batches, or across a single batch of material, i.e., wafer-to-wafer or within-wafer.

Variation in system parameters, i.e., metrology hardware and material parameters, can lead to inaccuracies in CD values, and any other parameters used to describe the structure under inspection, retrieved from optical metrology measurements. In particular, the library diffraction signals are calculated according to certain predefined parameters, often based on a particular set of hardware specifications under expected or average material and operating conditions. If the actual pieces of hardware and material used in the measurement of a sample's diffraction signal differ from those specifications and characteristics used in the library calculations, inaccuracies may occur when attempting to find a best-fit or match of the measured diffraction signal with the calculated library diffraction signals. Thus, because of such considerations, different instruments and materials typically require different libraries corresponding to the instrument and material specifications and characteristics.

BRIEF SUMMARY

In one exemplary embodiment, a method of generating sets of coefficients for use in optical metrology of semiconductor structures is provided. At least three simulated optical metrology signals for a set of parameters are obtained, where the simulated optical metrology signals are indicative of light diffracted from a semiconductor structure, and a value of at least one parameter of the set of parameters is varied to produce each signal. Functional relationships between the at least three simulated optical metrology signals are obtained, the functional relationships including at least three coefficient values. At least three sets of coefficients from the at least three coefficient values of the functional relationships are determined.

The present invention is better understood upon consideration of the detailed description below in conjunction with the accompanying drawings and claims.

DETAILED DESCRIPTION OF EXEMPLARY EMBODIMENTS

In order to provide a more thorough understanding of the present invention, the following description sets forth numerous specific details, such as specific materials, techniques, and the like. It should be recognized, however, that the description is not intended as a limitation on the scope of the present invention, but is instead provided to enable a better description of exemplary embodiments.

Figure 1:
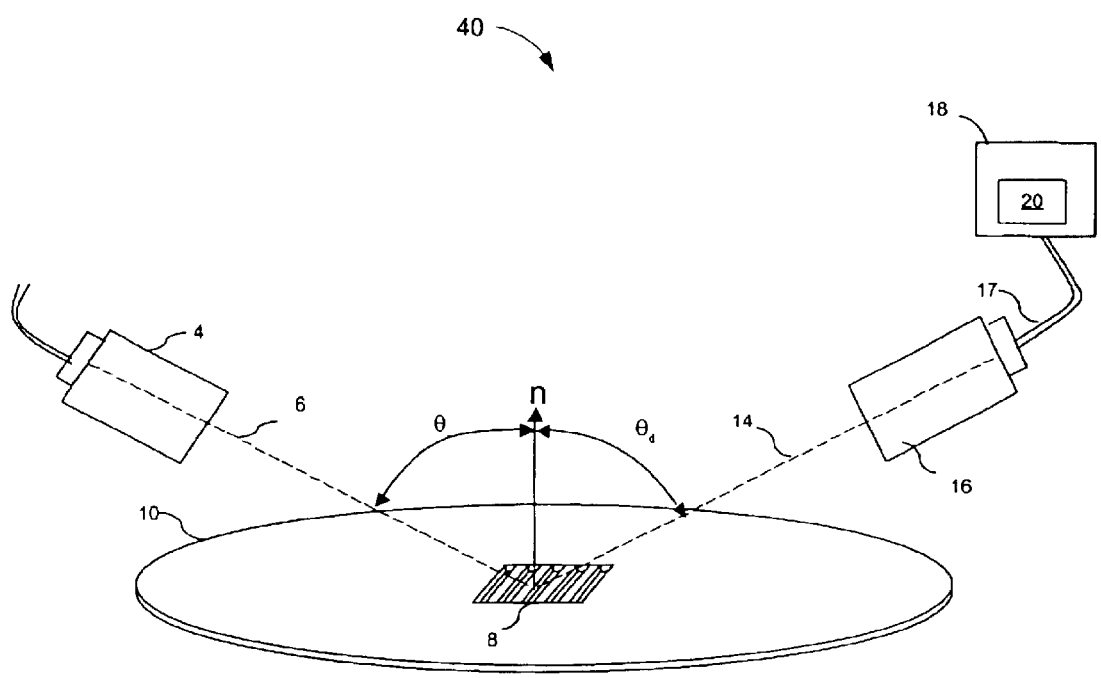
FIG. 1 illustrates an exemplary metrology system used to measure diffracted beams from semiconductor structures.

FIG. 1 illustrates an exemplary metrology system 40 used to measure metrology signals from a periodic structure 8 that may be included on a semiconductor wafer 10. It should be recognized that metrology system 40 can be used to measure metrology signals from various semiconductor structures on semiconductor wafer 10, such as integrated circuit (IC) structures, as well as other sample structures not on semiconductor wafer 10, such as a photomask, a liquid crystal display (LCD) panel, or the like.

In the exemplary embodiment depicted in FIG. 1, metrology system 40 includes a metrology beam source 4 projecting a metrology beam 6 at the target sample periodic structure 8. The metrology beam 6 is directed at an incidence angle $\theta_i$ from the normal towards the target structure 8 and diffracted at a diffraction angle $\theta_d$ from the normal. The diffracted beam 14 is received and measured by beam detector 16, which generates a measured metrology signal 17 based on the diffracted beam 14. Note that if light is used, the diffracted light can be propagated at different angles, depending on the pitch, incident angle, and wavelength. Additionally, diffracted light can be propagated at multiple orders at angles given by Bragg's equation.

The measured metrology signal 17 is provided to a metrology profiler system 18, generally a computerized system. The metrology profiler system 18 then compares the measured metrology signal 17 against a library of simulated metrology signals 20, which includes library instances of varying structural profiles and simulated metrology signals associated with the structural profiles. In one example, the library instance with the simulated metrology signal best matching the measured metrology signal 17 is selected. The structural profile associated with the matching simulated metrology signal is then assumed to correspond to that of the features of the target structure 8.

Additionally, each instance in library 20 can include a combination of a structural profile and a simulated metrology signal associated with the structural profile. Further, library 20 can include library instances representing varying structural profiles. For example, library 20 can include instances for simulated grating profiles having detailed profile characteristics, such as rounding, footing, T-topping, material thickness variation, sidewall angles, CD variations, and the like.

One such exemplary library based metrology system is an optical metrology system. In optical metrology systems, to determine the profile of a sample, an optical metrology signal is measured for the sample. The measured optical metrology signal can then be compared with a library of simulated optical metrology signals to determine a best match. The library of simulated optical metrology signals includes a number of possible profiles of the sample associated with the simulated optical metrology signals. Thus, the profile associated with the matching simulated optical metrology signal from the library can be taken to correspond to the actual profile of the sample. An exemplary optical metrology system is described in co-pending U.S. patent application Ser. No. 09/727,530 entitled "System and Method for Real-Time Library Generation of Grating Profiles" by Jakatdar, et al., filed on Nov. 28, 2000, and is incorporated in its entirety herein by reference. Other exemplary library based metrology systems include, for example, scanning electron microscopy (SEM) metrology systems or the like.

In an optical metrology system, the simulated optical metrology signals in library 20 can be generated using Rigorous Coupled-Wave Analysis (RCWA) techniques, as described in U.S. patent application Ser. No. 09/764,780 entitled "Caching of Intra-Layer Calculations for Rapid Rigorous Coupled-Wave Analysis," by Niu et al., filed Jan. 25, 2001, which is incorporated herein by reference in its entirety. It should be recognized that other simulation algorithms might also be used to generate the simulated optical metrology signals in library 20. An exemplary integral method is described in "Numerical Methods for the Analysis of Scattering from Nonplanar Periodic Structures", A. R. Neureuther and K. Zaki, Int'l URSI Symposium on Electromagnetic Waves, Stresa, Italy, pp 282-285, 1969, which is incorporated in its entirety herein. A differential method is described in "Systematic Study of Resonances Holographic Thin Film Coulers", M. Neviere et al, Optics Communications, Vol. 9, No. 1, pp 48-53, September 1973, which is incorporated herein by reference in its entirety.

The simulated optical metrology signals in library 20 can be generated using a set of parameters. The set of parameters can include one or more hardware device parameters that correspond to specific hardware-related parameters of the optical metrology system, such as angle of incidence of the metrology beam, numerical aperture, wavelength, input polarization, and the like. The set of parameters can also include one or more material parameters of the specimen, such as optical properties relating to the refractive index "n" and extinction coefficient "k", thickness values, and the like. Thus, the set of parameters used in generating the library can be predefined to correspond to particular metrology hardware specifications and/or material properties. Additionally, the library may be created according to the linearity criteria described in co-pending U.S. patent application Ser. No. 10/075,904 entitled "Profile Refinement for Integrated Circuit Metrology," by Junwei Bao, et al., filed on Feb. 12, 2002, which is incorporated herein by reference in its entirety.

The set of parameters used to generate a particular library for a particular optical metrology system, however, can differ from the parameters associated with the actual optical metrology system. For example, hardware parameters often vary between similar but different optical metrology systems. Additionally, hardware parameters can drift or vary within a single optical metrology system over time, such as with variations in temperature and humidity. Hardware parameters can also change when a part is replaced, such as a light source. Similarly, material parameters of the actual optical metrology system can also vary between different batches of wafers, or even at different locations of a wafer, due to environmental variables, such as changes in temperature, humidity, and the like, as well as fabrication variables, such as changes in process, chemistries, and the like.

Due in part to the variability of these parameters, a library generated for a particular optical metrology system may provide erroneous results when the library is used in the actual optical metrology system. For example, a library may be generated assuming a particular angle of incidence of the metrology beam. However, the angle of incidence of the metrology beam of the actual optical metrology system can differ from that used to generate the library. For example, when the bulb of a light source is changed, the effective angle of incidence can change by as much as 0.7 degrees from a variation in bulb features such as physical dimensions, overall light distribution, positioning, and the like. The change in the angle of incidence can produce erroneous results when matching measured optical metrology signals with the simulated optical metrology signals stored on the library.

In conventional optical metrology systems, such erroneous results may result in the library having to be regenerated, which can cause delay in the implementation and/or use of the optical metrology system. Alternatively, multiple libraries can be generated with each library having been generated using different sets of parameters. However, as noted earlier, this can make the library generation process more time and cost consuming, and inflexible as it may be difficult to anticipate potential variations in the parameters of concern.

Figure 2:
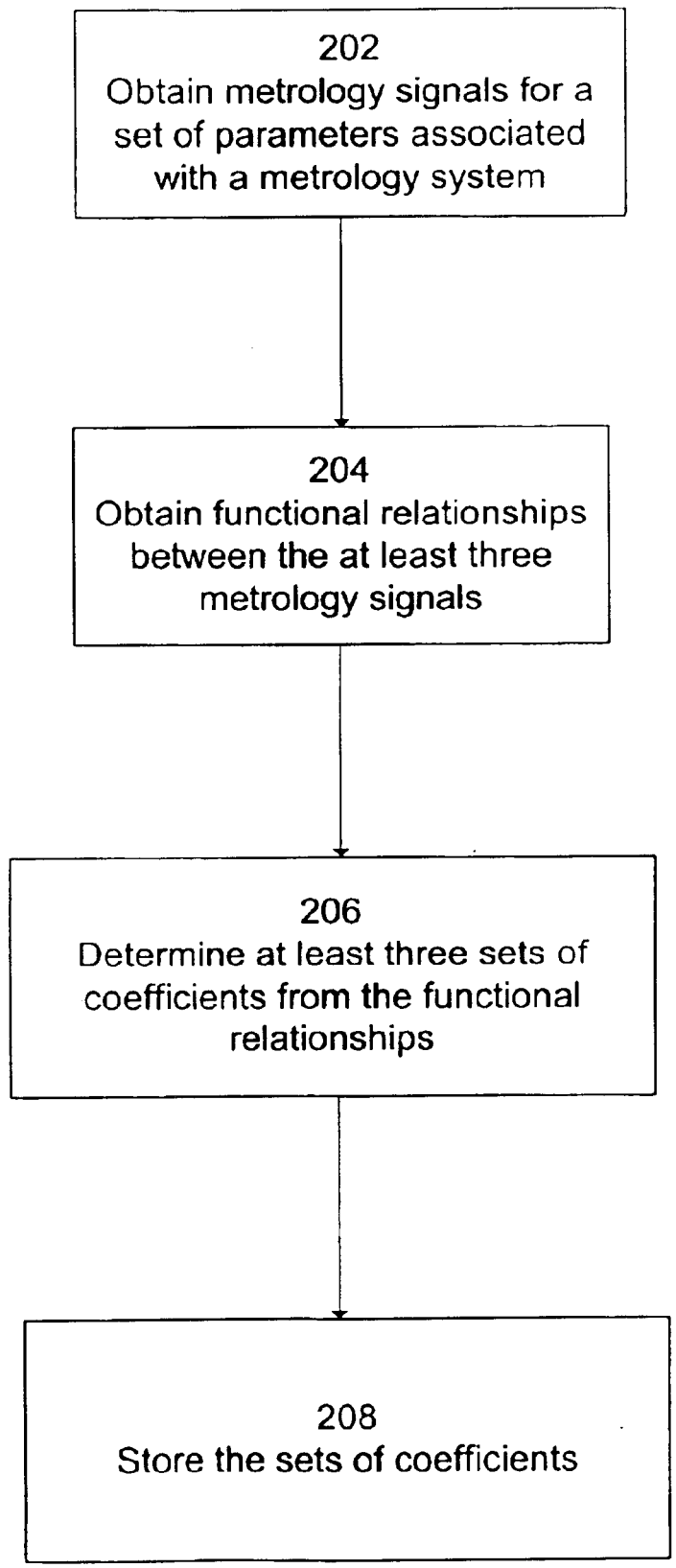
FIG. 2 is a flow chart of an exemplary process for modifying a library of simulated optical metrology signals.

Thus, in one exemplary embodiment, a set of coefficients is obtained for use in optical metrology of semiconductor structures. More particularly, with reference to FIG. 2 and block 202, in the present exemplary embodiment at least three simulated optical metrology signals are obtained for a set of parameters associated with a metrology system. Each signal is obtained with at least one of the set of parameter values being varied. At block 204, functional relationships are obtained between the at least three simulated optical metrology signals, where the functional relationships each include at least three coefficient values. At block 206, at least three sets of coefficients from the at least three coefficient values for different measurement points obtained at block 204 are determined. At block 208, the three or more sets of coefficients can then be stored.

The sets of coefficients can then be used to create or modify simulated optical metrology signals for different parameter values. As stated above, the set of parameters used to generate the simulated optical metrology signals can include hardware device parameters and material parameters. Further, one or more of the parameters of the set of parameters used to generate the simulated optical metrology signals can differ from that of the actual optical metrology system used. For example, the hardware device parameters of the actual optical metrology system can differ from those used to generate a library of simulated optical metrology signals. Similarly, the material parameters of the specimen can differ from those used to generate a library of simulated optical metrology signals. Thus, in the present exemplary embodiment, the sets of coefficients associated with the optical metrology system that are obtained can generate simulated optical metrology signals, including a library, for varying hardware device parameters and/or material parameters.

The exemplary method for generating sets of coefficients for use in optical metrology of semiconductor structures described above obtains at least three simulated optical metrology signals for a set of parameters. As will be described in greater detail below, one exemplary process includes storing sets of coefficients for creating a library of simulated optical metrology signals based on the sets of coefficients and actual metrology system parameters. Another exemplary process includes storing sets of coefficients for adjusting simulated optical metrology signals of a previously stored library of simulated optical metrology signals based on a change in at least one parameter of the metrology system. The created or adjusted libraries of the two embodiments can then be used to compare a measured optical metrology signal with the stored library of simulated optical metrology signals. Further, the libraries can be replaced or further adjusted with the stored sets of coefficients as parameters vary over time, without the need to regenerate the library off-line or store multiple libraries for multiple parameter values.

With reference to FIG. 1, in one exemplary embodiment, metrology profiler system 18 can be configured to obtain and use the sets of coefficients as part of metrology system 40. More particularly, when metrology system 40 is configured for optical metrology of semiconductor structures, metrology system 40 can include a source 4 configured to direct an optical metrology beam at a semiconductor structure. Metrology system 40 can also include a detector 16 configured to receive the optical metrology beam diffracted from the semiconductor structure and generate an optical metrology signal based on the optical metrology beam. Metrology profiler system 18 can be configured to receive the optical metrology signal from detector 16 (i.e., a measured optical metrology signal). Metrology profiler system 18 then can compare the measured optical metrology signal to a library of simulated optical metrology signals, which was created or adjusted based on stored sets of coefficients as described above.

Figure 3:
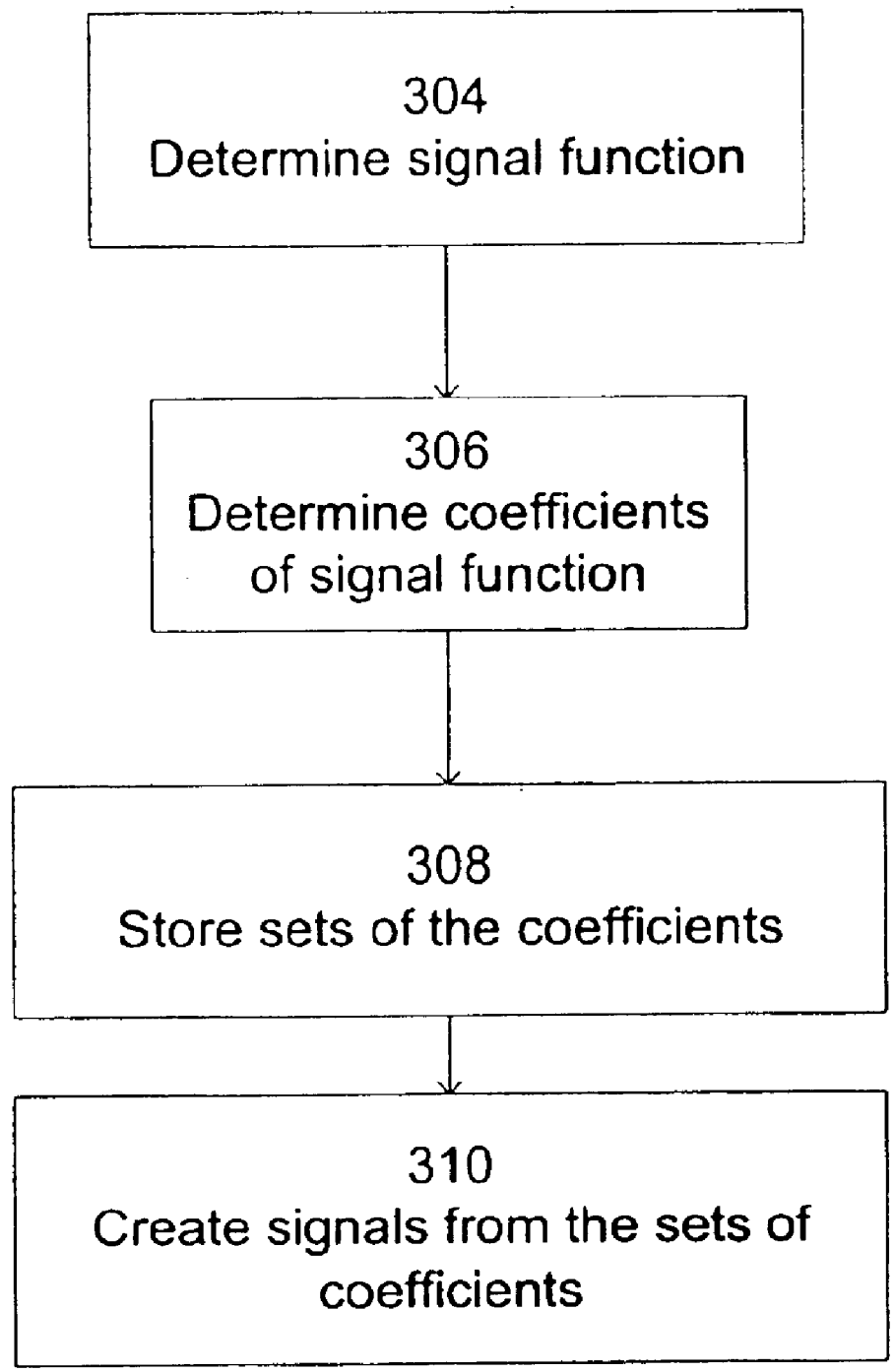
FIG. 3 is a flow chart of an exemplary process for varying a particular library for different parameters.

With reference to FIG. 3, an exemplary process of generating sets of coefficients based on metrology system parameters that can be stored in place of multiple libraries of optical signals is depicted. For the sake of example, assume that the sets of coefficients will be generated for a difference between one parameter (parameter P) associated with the optical metrology system. Parameter P can include a hardware device parameter or a material parameter. It should be noted that the sets of coefficients can be based on more than one parameter, such as two or more hardware device parameters, material parameters, and/or combinations of hardware device and material parameters. In the present exemplary embodiment, when sets of coefficients are generated for multiple parameters, sets of coefficients are generated for each parameter separately then combined.

At block 304, simulated optical metrology signals are calculated at different measurement points, such as wavelengths, angles of incidence, a hybrid of the two, or the like for different values of parameter P. For the sake of example, assume that the different measurement points are wavelengths. The different values of parameter P are determined, for example, by first determining the nominal range of the instrument for the parameter P. The nominal range of the instrument is generally the range over which the instrument will likely vary or drift over time, $P \pm \delta$, where $\delta$ is the one-sided range of the likely change or drift over time in P. The nominal range could also be the likely range of different instruments that will use sets of coefficients. Further, the signals may include measurement points at a number n of wavelengths $\lambda$, within the range of wavelengths used by the particular instrument. A signal function can then be fit to the simulated optical metrology signals at a particular measuring point. The function can be expressed, for example, by a second order polynomial, such as:

$$S = f(P) = \alpha P^2 + \beta P + \gamma \quad (1)$$

where $\alpha$, $\beta$, and $\gamma$ are coefficients of the polynomial signal function. It should be noted, however, that the second order polynomial function is used here for illustrative purposes only and that higher order polynomials may be used depending on the application and desired accuracy. Further, other functional relationships, such as a series of Fourier functions, spline functions, or the like may be used in a similar fashion.

Figure 4A:
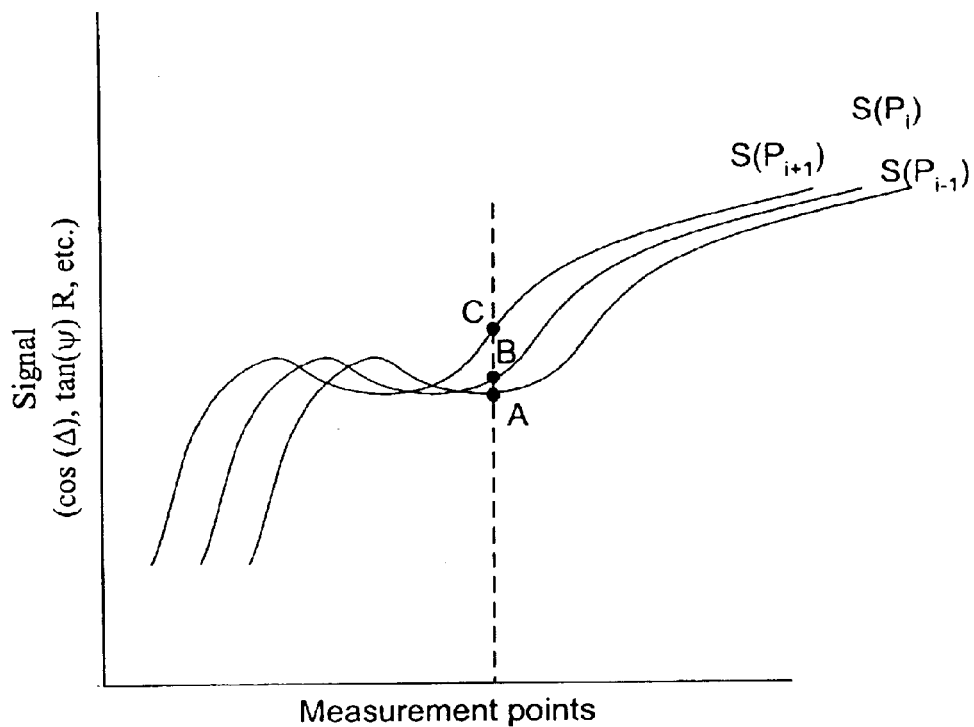
FIGS. 4A and 4B are graphs illustrating exemplary signals and a signal function respectively.
Figure 4B:
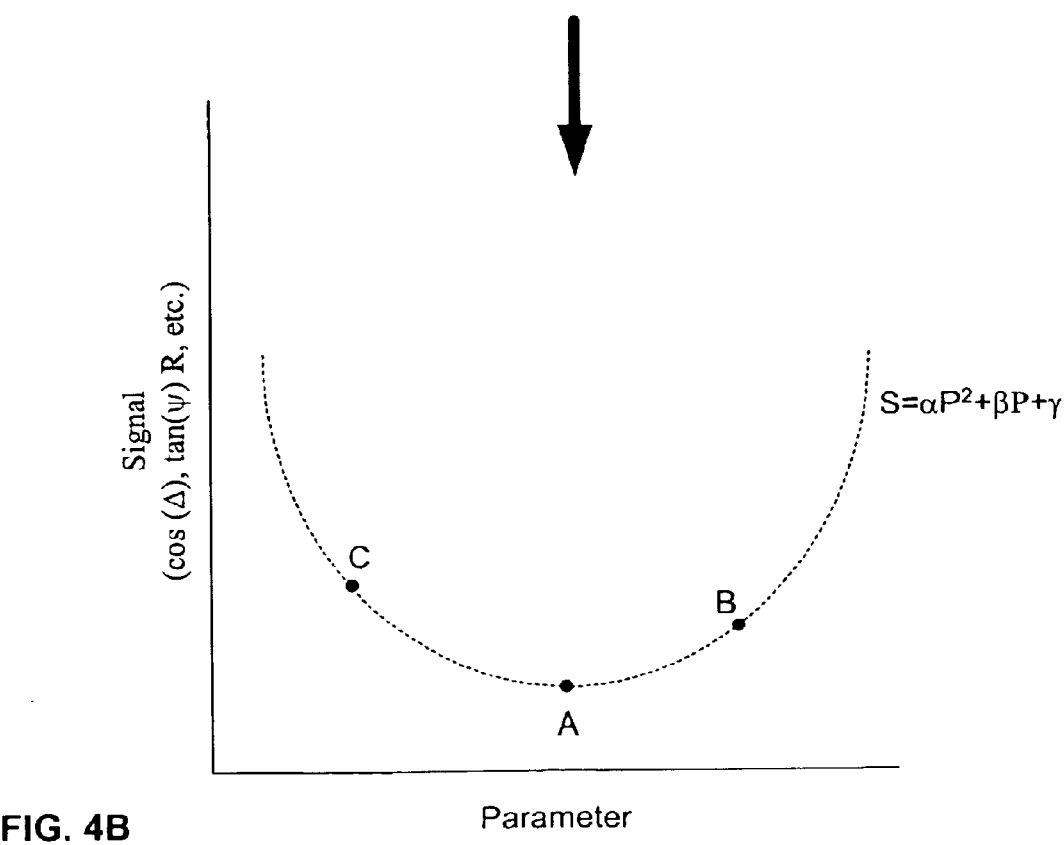

FIGS. 4A and 4B are graphs illustrating exemplary simulated optical metrology signals and a signal function respectively. As illustrated in FIG. 4A, three simulated optical metrology signals can be created within a nominal range of the parameter, i.e., at the nominal parameter P, P+δ', and P−δ', where δ' is typically less than or equal to δ. FIG. 4A illustrates an exemplary graph of signals for the three polynomials produced for a large number n of wavelengths λ within a range of wavelengths for the particular set of parameters. FIG. 4B illustrates an exemplary graph of a signal function for parameter P at a particular measurement point. The output variable is, for example, ellipsometric values cos(Δ) and tan(ψ), the reflectance R, or other such output variable that is being measured depending on the particular instrument and/or application.

With reference again to FIG. 3, at block 306, the value of the coefficients, α, β, and γ in the polynomial function are then determined for each wavelength in the range, i.e., each measurement point. The coefficient values can then be stored as sets of coefficients.

A more general interpolation can be performed of the three simulated optical metrology signals produced for each of P, P+δ', and P−δ', at every wavelength in the particular range. This results in other sets of coefficients for each wavelength. For the sake of example, assume that there are three sets of coefficients as with a choice of polynomial of the second order:

$$\alpha(\lambda) \quad (2)$$

$$\beta(\lambda) \quad (3)$$

$$\gamma(\lambda) \quad (4)$$

At block 308, the sets of coefficients, in this example sets $\alpha(\lambda)$, $\beta(\lambda)$, and $\gamma(\lambda)$, can then be stored in place of a multitude of alternatively generated libraries for different parameter values. At block 310, when the value of parameter P is obtained, the previously created sets of coefficients $\alpha(\lambda)$, $\beta(\lambda)$, and $\gamma(\lambda)$ related to parameter P can be retrieved and applied to generate simulated optical metrology signals or a library of simulated optical metrology signals for the particular value of parameter P. The generated signal or library from the sets of coefficients is a close approximation of a stored library with the new parameters. The new simulated optical metrology signal or adjusted library can then be compared to an optical metrology signal measured by the instrument (i.e., a measured optical metrology signal).

It should be recognized that numerous modifications can be made to the process depicted in flow chart described above. For example, a higher order polynomial may be used in equation (1) depending on the application, as well as other equation such as series of Fourier functions, spline functions, and the like. Additionally, each block of the flow chart can include many processes not explicitly described. Further, the process can be applied to various parameters such as the angle of incidence, numerical aperture, sample material characteristics, and the like.

Figure 5:
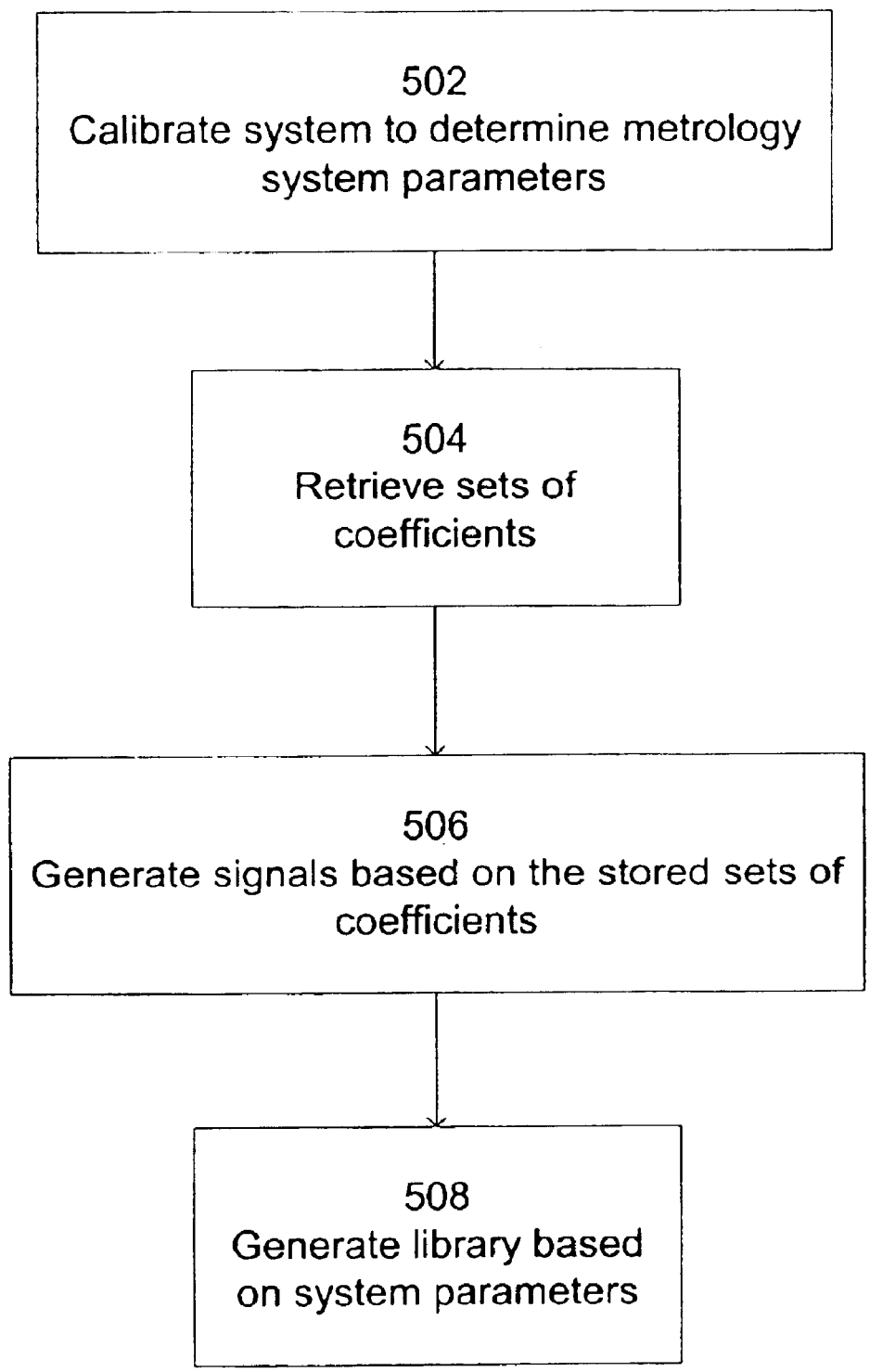
FIG. 5 is a flow chart of an exemplary process for varying a particular library for different parameters.

FIG. 5 illustrates a flow chart describing an exemplary method of calibrating an optical metrology system and creating simulated optical metrology signals or a library after the library of coefficients, i.e., sets of coefficients, have been created and stored. At block 502, the optical metrology system is initially calibrated to obtain one or more parameters associated with the optical metrology system. The one or more parameters can then be included in a set of constants that is used by the optical metrology system during operation and measurements. At block 504, the optical metrology system then retrieves the stored sets of coefficients $\alpha(\lambda)$, $\beta(\lambda)$, and $\gamma(\lambda)$. At block 506, the optical metrology system can then create simulated optical metrology signals for each point in a library using equation (1) based on the obtained one or more parameters from the set of constants, and the stored sets of coefficients, i.e., sets $\alpha(\lambda)$, $\beta(\lambda)$, and $\gamma(\lambda)$.

The adjusted optical metrology signal created at block 506 is a simulated optical metrology signal, i.e., signal function S of equation (1), which has been customized to the parameters corresponding to the particular piece of metrology hardware and material batches being used according to the stored sets of coefficients. Thus, at block 508, a complete or partial library of simulated optical metrology signals based on the actual parameters can be created for use with the particular optical metrology system, including the hardware and materials used in the particular optical metrology system.

It should be recognized that numerous modifications can be made to the process depicted in the flow chart described above. For example, block 504 could be performed prior to block 502, i.e., the sets of coefficients could be retrieved prior to obtaining the parameters. Additionally, each block can include many processes not explicitly described. Further, metrology signals other than optical metrology signals can be used, such as electron metrology signals in SEM.

Figure 6:
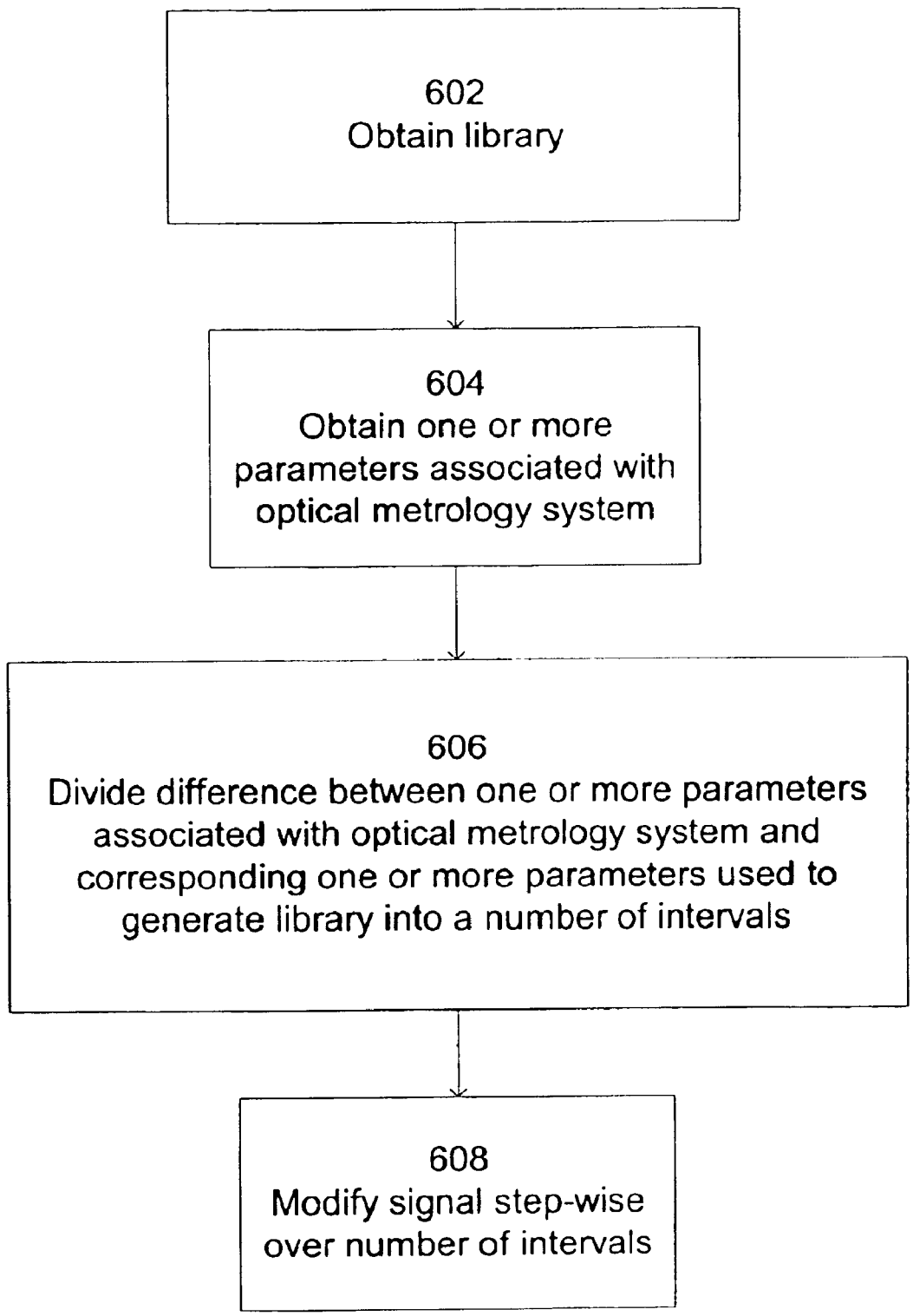
FIG. 6 is a flow chart of an exemplary process for adjusting a library of simulated optical metrology signals.

With reference to FIG. 6, another exemplary process for generating sets of coefficients for use in optical metrology is depicted. In this example, the sets of coefficients are used to adjust an initial library of simulated optical metrology signals for changes in parameters. Again, for the sake of example, assume that the library of simulated optical metrology signals will be adjusted based on a difference between one parameter (parameter P) associated with the optical metrology system that was obtained and the corresponding parameter P in the set of parameters used to generate the library of simulated optical metrology signals. As described above, parameter P can include a hardware device parameter or a material parameter. It should be noted again that the library of simulated optical metrology signals can be adjusted based on more than one parameter, such as two or more hardware device parameters, material parameters, and/or combinations of hardware device and material parameters. In the present exemplary embodiment, when sets of coefficients are generated for multiple parameters, the sets of coefficients can be generated for each parameter separately then combined, or generated all at once for the multiple parameters.

At block 602, a library of simulated optical metrology signals is obtained. The library of simulated optical metrology signals is generated using a set of parameters that can correspond to particular metrology hardware specifications and/or material properties.

At block 604, one or more parameters associated with the optical metrology system are obtained. As described above, for the sake of example, assume parameter P associated with the optical metrology system is obtained. Additionally, assume that the obtained value of parameter P differs from the value of parameter P when the library of simulated optical metrology signals was generated.

At block 606, the difference between the one or more parameters associated with the optical metrology system and the corresponding one or more parameters used to generate the library is divided into a number of intervals. At block 608, a simulated optical metrology signal from the library can be adjusted step-wise over the number of intervals to obtain an adjusted simulated optical metrology signal for the one or more parameters associated with the optical metrology system. As described below, the number of intervals can depend, in part, on the desired accuracy.

Again for the sake of example, assume that the library was originally generated using a set of parameters including parameter P with an initial value (i.e., $P_o$). Assume also that when the library is used, the actual value for parameter P (i.e., $P_n$) is determined to differ from $P_o$. Thus, the difference between $P_o$ and $P_n$ is divided into a number of intervals (i.e., N). A simulated optical metrology signal from the library corresponding to the initial value of parameter P ($P_o$) can then be adjusted step-wise over the number of intervals (N) to obtain an adjusted simulated optical metrology signal for the actual value of parameter P ($P_n$).

In the present exemplary process, the simulated optical metrology signal is adjusted step-wise over a number of intervals based on a relationship between a change in the simulated optical metrology signals and a change in the one or more parameters associated with the optical metrology system. Thus, in the example described above, the simulated optical metrology signal is adjusted based on a relationship between a change in the simulated optical signals and a change in parameter P.

In one exemplary embodiment, the relationship between changes in simulated optical metrology signals and one or more parameters is characterized by a Jacobian matrix. Thus, in this embodiment, using the example described above of parameter P, the simulated optical metrology signals can be adjusted step-wise over a number of intervals according to the following algorithm:

$$S_0 =_t S(P_0) \qquad (5)$$

For i=0 to N-1 $S_{(i+1)} = S_i + J(P_i)*(P_{i+1} - P_i)$

Next i $$S_{new}(P_N) = S_N$$

where $J(P_i)$ is a Jacobian matrix that can be evaluated at each step-wise iteration from $P_o$ to $P_n$. Thus, a change in the optical metrology signal is related to a change in parameter P over a small, approximately linear, change in the parameter. After successive linear steps or iterations of equation (5) above, the final calculated $S_{new}$ will be a close approximation to an exactly computed signal at $P_n$ determined with a simulation method, such as RCWA or other rigorous method.

Figure 7:
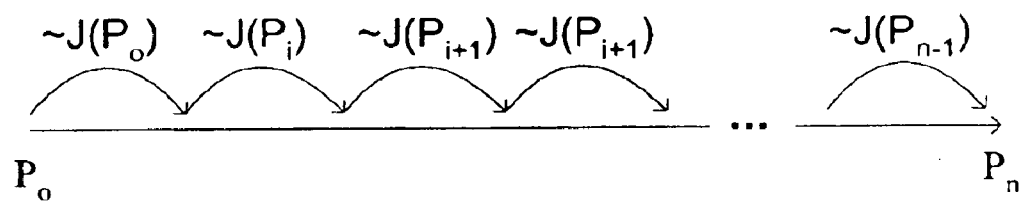
FIG. 7 is a graphical representation of exemplary stepwise iterations used for adjusting a particular library for different parameters.

The iteration steps from $P_o$ to $P_n$ are shown graphically in FIG. 7 by the curved arrows. Because the Jacobian matrix J is typically only accurate over small changes in a parameter, each step is sufficiently small to ensure the desired level of accuracy for parameter $P_n$. The number of iterations performed, for example, can be greater than 40, preferably greater than 50, or more step-wise iterations between $P_o$ to $P_n$. As more iterations are performed, the error is accordingly reduced. It is typically desired to perform a number of iterations to reduce the error between the reconstructed signals and the ones that would have been obtained using accurate simulations to or near the instrument noise. The desired accuracy and the difference between $P_o$ to $P_n$ determine the optimal number of iterations for a given application.

As described below in greater detail, partial derivatives of the optical metrology signal are used in the Jacobian matrix. In one exemplary embodiment, these partial derivatives can be estimated using a polynomial approximation, which can be pre-computed and stored. Thus, during each iteration of equation (5) above, in the present exemplary embodiment, the polynomial approximation can be used rather than recalculating the partial derivatives for the Jacobian matrix.

Figure 8:
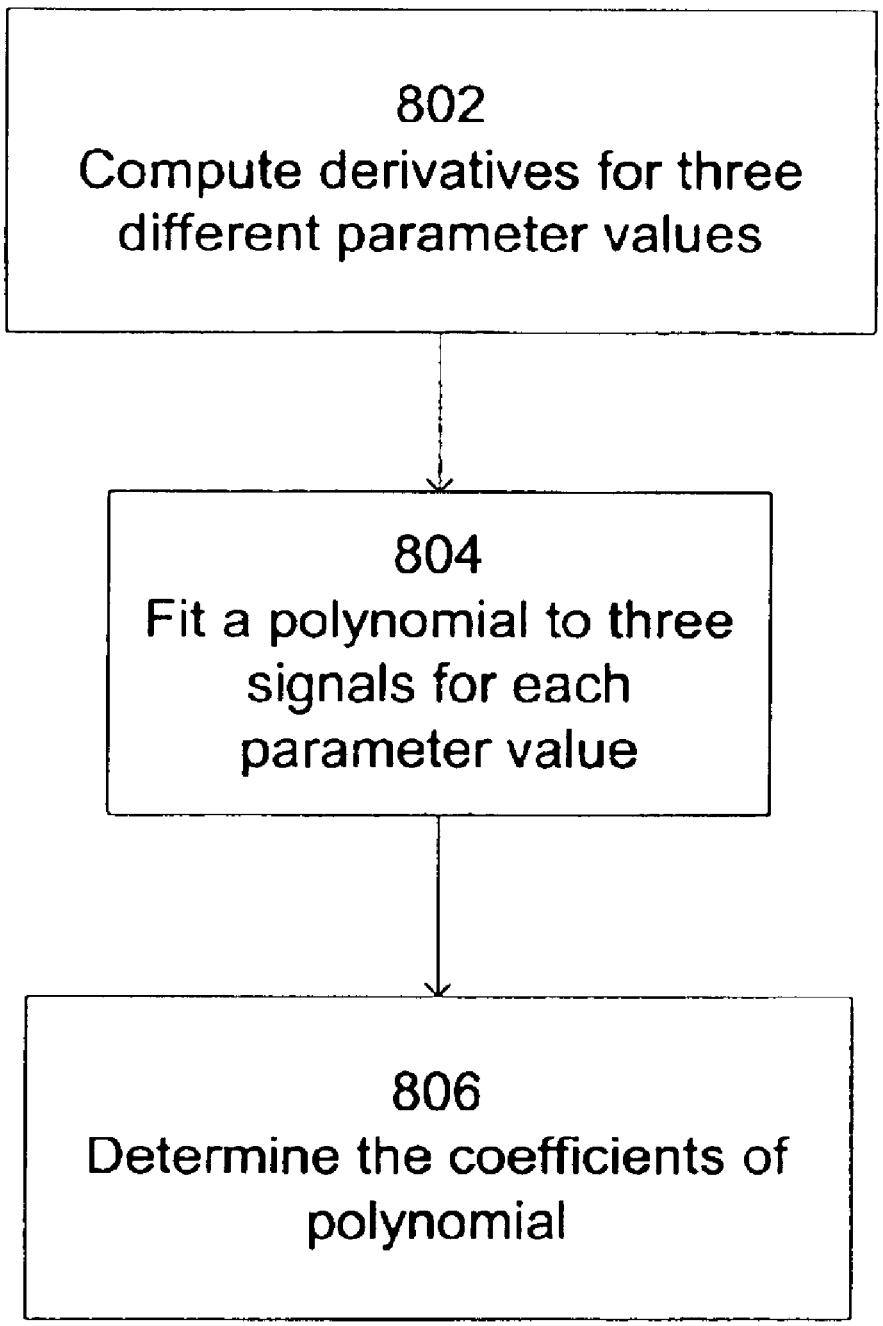
FIG. 8 is a flow chart of an exemplary process of determining a polynomial approximation of partial derivatives.

More particularly, with reference to FIG. 8, at block 802, in order to approximate derivatives for various parameters used in the Jacobian matrix, derivatives are computed of simulated optical metrology signals for at least three different parameter values. For example, derivatives are computed for parameter P at $P_o$, $P_{o-1}$, and $P_{o+1}$. At block 804, a second order polynomial is fit through the three signals at each wavelength within the range of wavelengths measured. The polynomial function coefficients will then provide an approximation of the derivative of a signal function at any parameter P. The process is performed similar to that in the previous example as described with respect to FIGS. 4A and 4B. In this example, however, to create sets of polynomials from functional relationships between the three simulated optical metrology signals the at least three simulated optical metrology signals are derivatives of the signal with respect to parameter P. The functional relationship between the three signals at a measuring point can be similar to equation (1), and where sets of coefficients can be determined at block 806.

It should be noted that a greater number of simulated optical metrology signals and/or higher order polynomials can be used depending on the application and desired accuracy. Additionally, other functional relationships, such as a series of Fourier functions, spline functions, or the like may be used in place of a second order polynomial. Further numerous modifications can be made to the process depicted in flow chart described above. For example, a higher order polynomial may be used in equation (1) depending on the application and desired accuracy. Additionally, each block can include many processes not explicitly described. Further, metrology signals other than optical metrology signals can be used, such as electron metrology signals in SEM.

Figure 9:
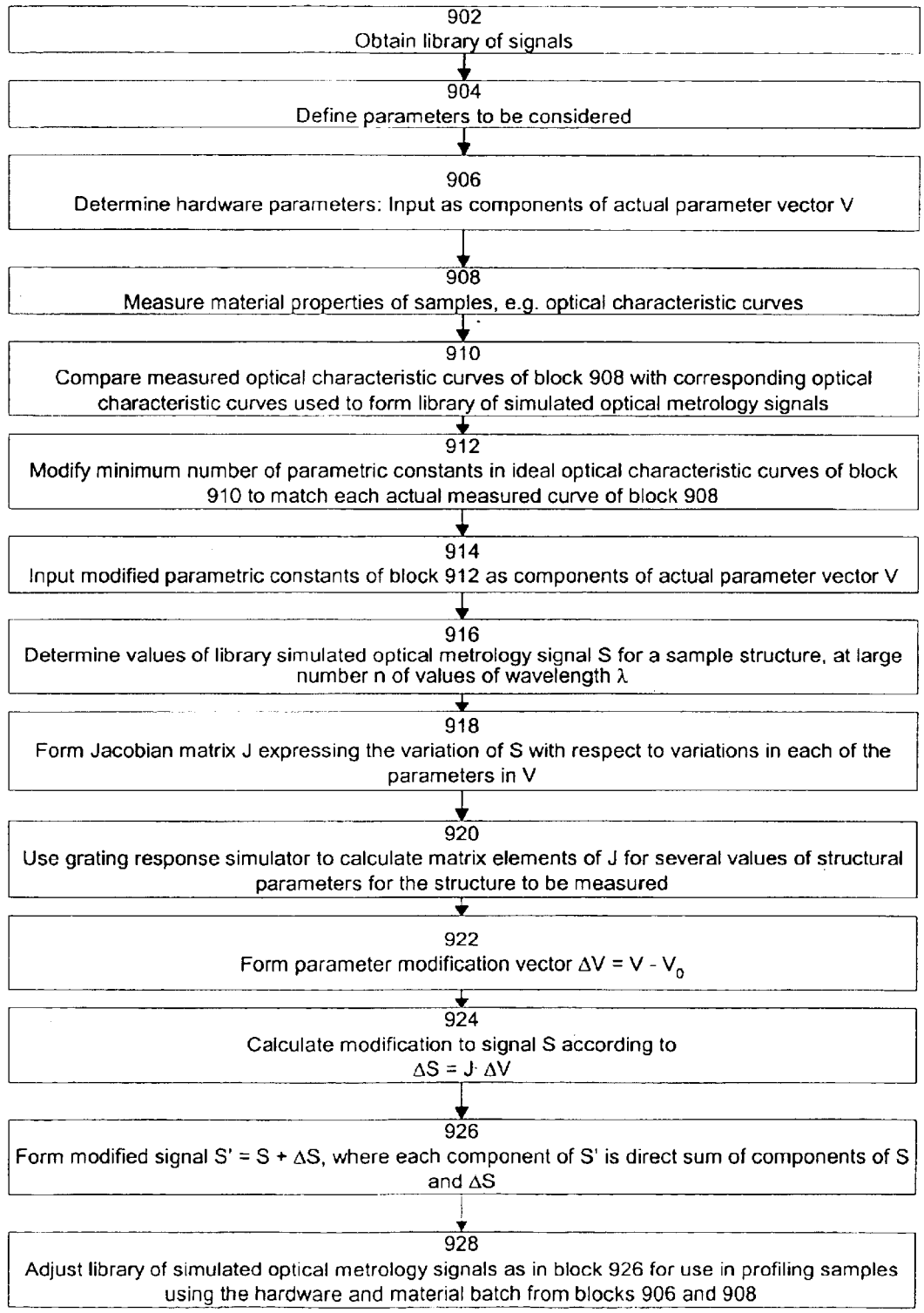
FIG. 9 is a flow chart of an exemplary process for using a matrix to account for multiple varying parameters of a particular library.

FIG. 9 illustrates a more detailed flow chart of an exemplary process for calculating the Jacobian matrix applicable for any number of varying parameters between the library and the particular hardware device and materials that can be used.

At block 902, a library of simulated optical metrology signals for an initial set of parameters is provided. As stated above, the simulated optical metrology signals are, for example, generated using the initial set of system parameters that include both hardware device parameters and material parameters.

At block 904, the variable parameters to be considered are defined. In the previous example, only one parameter was described as a variable parameter, however, more than one varying parameter can be considered. The varying parameters may include, but are not limited to, optical material-related parameters such as those used to describe material properties (e.g., optical characteristics n and k), sample surface roughness, and metrology hardware-related parameters such as numerical aperture, angle of incidence, resolution, polarization, and azimuthal angle of incidence with respect to the grating direction and the like. Each of these parameters is used by a grating response simulator to calculate the simulated optical metrology signals.

At block 906, the actual values of the hardware device parameters for the particular piece of metrology hardware to be used are determined. They may be determined according to the manufacturer specifications or calibrated by (or input) into the instrument. These parameter values are provided, for example, as components of an actual parameter vector V.

At block 908, the parameters are determined for all material properties of the sample to be measured. Such material properties include optical characteristics defined at block 902, as a function of wavelength γ across the wavelength range used in the optical metrology measurements. For example, n vs. γ and k vs. γ curves are measured for the particular batch of material to be profiled.

At block 910, the measured optical-characteristic curves of block 908 are compared with corresponding optical-characteristic curves from which the library of simulated optical metrology signals is formed. The optical-characteristic curves from the library can be expressed in parametric equation forms, which are known in the art and which generally contain parametric constants. By way of example, one form of an optical-characteristic equation for index of refraction n is a Cauchy equation wherein n is expressed as:

$$n(\lambda) = K_0 + K_2/\lambda^2 + K_4/\lambda^4 \tag{6}$$

where $K_0$, $K_2$, $K_4$ are parametric constants.

A similar equation can be formed for the extinction coefficient k wherein k is expressed as:

$$k(\lambda) = K_1/\lambda + K_3/\lambda^3 + K_5/\lambda^5 \tag{7}$$

In this case, an index of refraction curve used in the formation of the library of simulated optical metrology signals is obtained from an optical-characteristic equation:

$$n_0(\lambda) = K_{00} + K_{20}/\lambda^2 + K_{40}/\lambda^4 \tag{8}$$

where $K_{00}$, $K_{20}$, $K_{40}$ are parametric constants, which vary from material to material, and which are used as parameters to compute the library.

At block 912, the fewest possible number of parametric constants or functions $K_n$ in each optical-characteristic equation of block 912 is adjusted in order to match the optical-characteristic curves to the actual measured curves of block 908. For example, if the library n vs. λ curve can be sufficiently matched to the actual measured n vs. λ curve by adjusting only $K_0$ and $K_2$, then only those two inputs to the library need be considered as parameters relating to n. The degree of match considered sufficient can be user-determined based on the particular application. The adjusted K's are the actual rather than the library parametric values for the particular material batch. Methods for extracting parameter values from measured curves for materials characteristics such as n and k are known in the art. An example of such methods is found in "*An Integrated System of Optical Metrology for Deep Sub-Micron Lithography*", Xinhui Niu, PhD Thesis, Memorandum No. UCB/FRL M99/27, 1999, *University of California at Berkeley*, Chapters 3 and 4, which is incorporated herein by reference in its entirety.

At block 914, all adjusted parametric constants or functions of block 912 can be included as further components of the actual parameter vector V of block 906. By way of example, if only angle of incidence (AOI), numerical aperture (NA), and index of refraction parametric constants $K_0$ and $K_2$ were parameters that varied between materials batches and between pieces of metrology hardware, the actual parameter vector could be written as $$V = (AOI, NA, K_0, K_2) \tag{9}$$

It should be noted, however, that more or fewer components to the actual parameter vector could be considered. The $j^{th}$ parameter in the parameter vector is called $p_j$. In the aforementioned example, AOI is $p_1$, NA is $p_2$, $K_o$, is $p_3$, and $K_2$ is $p_4$.

At block 916, values of a simulated optical metrology signal are determined, i.e., signal function S (which has been calculated by the grating response simulator) for a sample structure (which may correspond to a library building-block structure, or may correspond to an actual structure to be measured) at a large number n values of wavelengths λ. For example, the number n may be greater than 40, preferably 50 or more, across the range of wavelengths λ used. S then has n components, denoted as:

$$S_1 = S(\lambda_1), \ldots S_n = S(\lambda_n) \tag{10}$$

At block 918, a Jacobian matrix J is formed expressing the variation of S with respect to variations in V, i.e., variations in any or all of the parameters in the parameter vector V. For example, if V were that of the example of block 914, the Jacobian matrix would be of the form:

$$J = \partial S / \partial V = \begin{pmatrix} \frac{\partial S_1}{\partial (AOI)} & \frac{\partial S_1}{\partial (NA)} & \frac{\partial S_1}{\partial K_0} & \frac{\partial S_1}{\partial K_2} \\ \frac{\partial S_2}{\partial (AOI)} & \frac{\partial S_2}{\partial (NA)} & \frac{\partial S_2}{\partial K_0} & \frac{\partial S_2}{\partial K_2} \\ & \vdots & & \\ \frac{\partial S_n}{\partial (AOI)} & \frac{\partial S_n}{\partial (NA)} & \frac{\partial S_n}{\partial K_0} & \frac{\partial S_n}{\partial K_2} \end{pmatrix} \tag{11}$$

where $$\frac{\partial S_i}{\partial p_j}$$

is the partial derivative of the $i^{th}$ component of S, i.e., the value of S at wavelength value i, with respect to parameter $p_j$.

At block 920, using a grating response simulator, the matrix elements of J are calculated for several grid points corresponding to different values of the structural parameters for the sample structure.

Figure 10A:
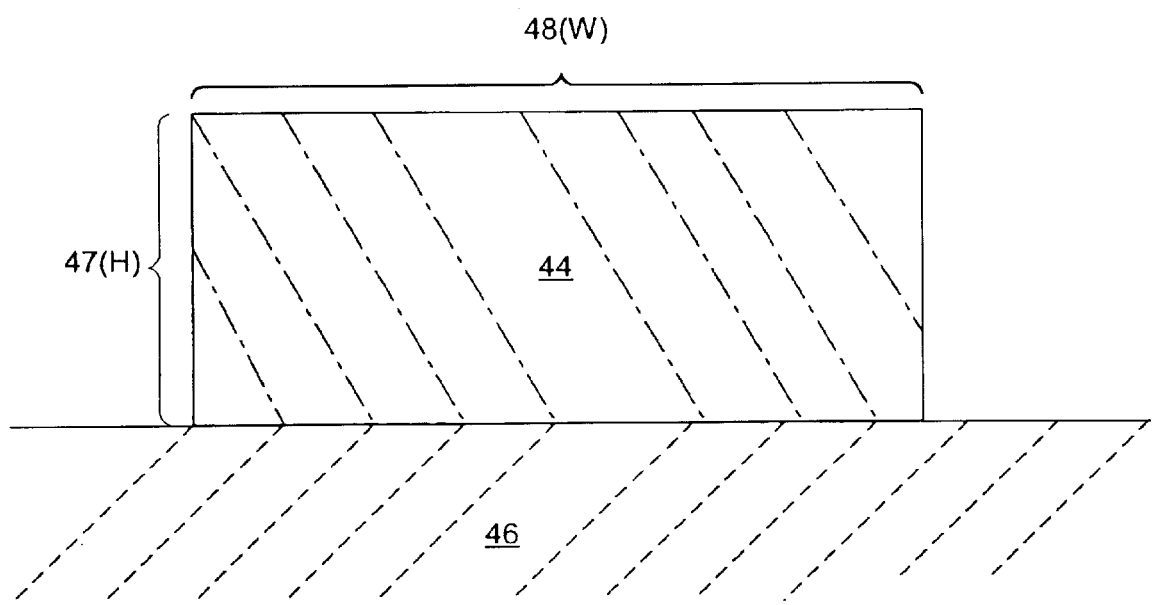
FIGS. 10A and 10B show an exemplary structural profile and an exemplary grid of profile parameter values respectively.
Figure 10B:
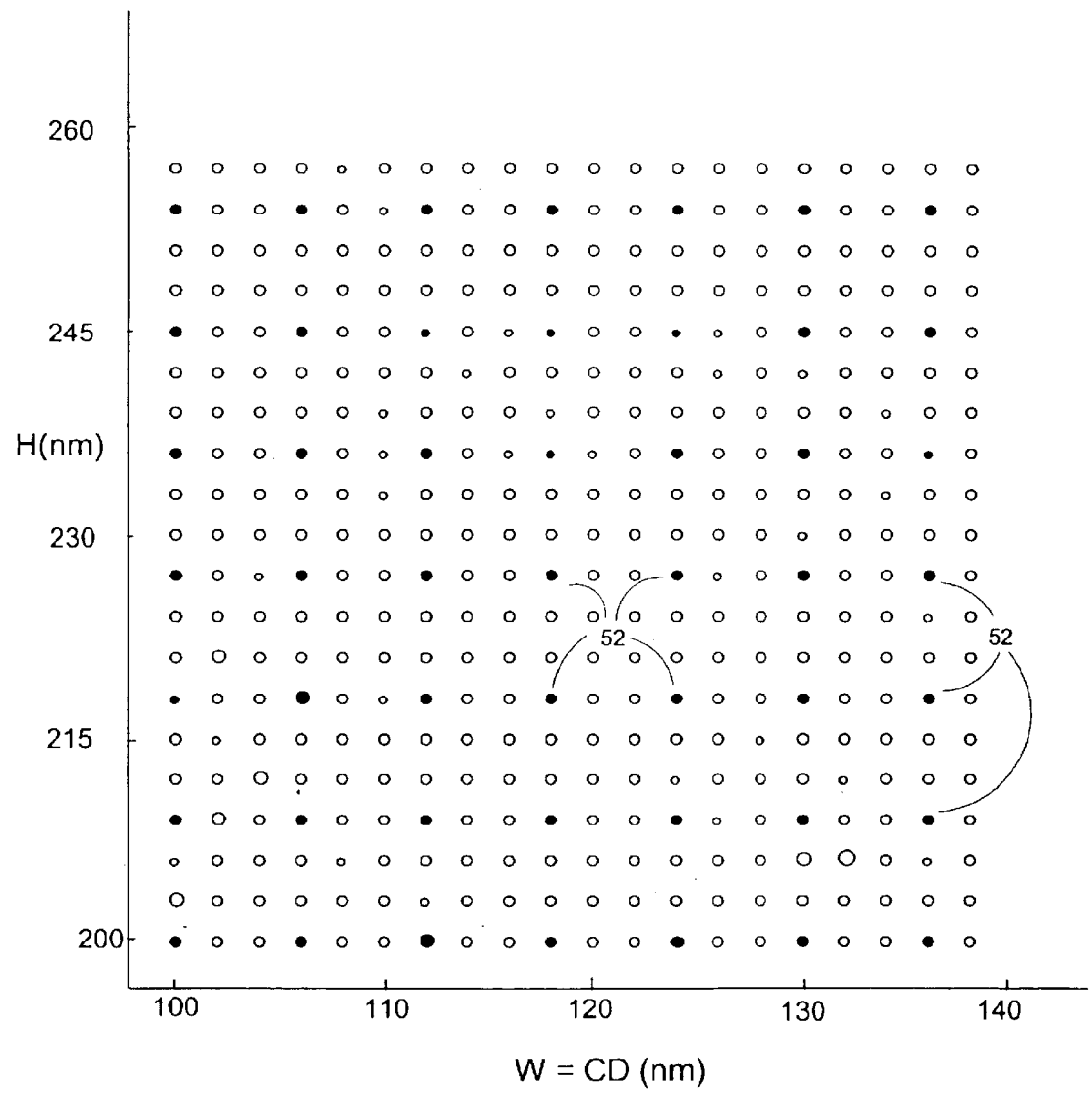

For example, with reference to FIG. 10A, assume a structure 44 has been formed on a layer 46, which can be a substrate or a layer formed previous to structure 44. Assume also that structure 44 has a height 47 (H) and width 48 (W). Now assume that FIG. 10B depicts grid points corresponding to values of H and W for which a simulated optical metrology signal has been calculated. In this example, the range of W is between 100 to 140 nm, and simulated optical metrology signals have been calculated for W values at 2 nm spacing, and the range of H is between 200 to 260 nm with simulated optical metrology signals calculated for H values at 3 nm spacing.

As described above, matrix elements of J for several J-matrices corresponding to points in a grid composed of a range of values of H and W are calculated. Assume in this example that the J matrix elements are calculated for every third grid point in each dimension, wherein matrix elements of J matrices corresponding to grid points 52 are calculated. Note that sampling only a portion of the grid points can significantly reduce the calculation time, however, the accuracy can suffer if the J matrix substantially varies in a small area of the grid.

Each partial derivative in the J matrix is approximated by varying a parameter, $K_0$ by way of example, a small amount called $\Delta K_0$, then calculating $\Delta S_i$, the change in the signal function $S(\lambda_i)$ due to the change in $K_0$. $\partial S_i/\partial K_0$ is approximated to be equal to $\Delta S_i/\Delta K_0$. The variation of the parameters is chosen sufficiently small so that the linear response relation is an accurate approximation. Determination of the maximum parameter variation to satisfy the linearity requirement to a specified extent can be performed using the methods described in co-pending U.S. patent application Ser. No. 10/075,904 entitled "Profile Refinement for Integrated Circuit Metrology," filed on Feb. 12, 2002, which is incorporated by reference herein in its entirety.

With reference again to FIG. 9, at block 922, subtract from each component of the actual parameter vector V the corresponding component of vector $V_0$, which includes parameters used in the formation of the library of simulated optical metrology signals. By way of example, if the parameter vector V were that of the example of block 914, the subtraction would be of the form:

$$\Delta V = V - V_0 = (AOI - AOI_0, NA - NA_0, K_0 - K_{00}, K_2 - K_{20}) \quad (12)$$

where $\Delta V$ is termed the parameter modification vector. The parameter vector $\Delta V$ is the change for each step between the library parameter value and the actual parameter value. In one example, a common number of steps is chosen for which each parameter range is divided. It should also be noted that each parameter could be changed separately with varying numbers of steps, or a few at a time, or as described in this example all at the same time.

At block 924, calculate a signal modification $\Delta S$ by matrix multiplication of the Jacobian matrix J by the parameter modification vector $\Delta V$:

$$\Delta S = J \cdot \Delta V \quad (13)$$

where $\Delta S$ is a vector with the same number of components as S, for example 50. Further, $\Delta S$ corresponds to a single iteration or step in equation (5) described above. Thus, the Jacobian matrix is applied for each successive iteration from the old to new parameter values as graphically illustrated, for example, in FIG. 7.

Referring again to block 920 and FIGS. 10A and 10B, the signal modification for any library profile is determined using the calculated J matrix at the grid point closest to that of the library profile. For example, in order to adjust the simulated optical metrology signal for a profile with W=128 nm and H=254 nm, the J matrix calculated at W=126 nm and H=257 nm would be used.

The J matrix elements can be calculated for each of the building block process structures and stored in a database. The J matrix elements can be calculated corresponding to the likely parameters, which might be variable, for example, using more than two K's to match the actual n vs. λ curve to the library based curve. Then in a real situation, the subset of those elements, which are to be included are determined, and the extraneous matrix elements corresponding to the parameters not included are set to zero, thereby having no effect on $\Delta S$. Alternatively, the $\Delta p$'s of extraneous parameters can be set to zero in the $\Delta V$ vector. Either of these approaches allows for a simple transformation between various pieces of metrology hardware and material batches; only the parameter modification vector will need to be determined and the matrix multiplication performed.

Additionally, the database can be expanded to include a library of J matrix elements encompassing a spectrum of values for each metrology hardware and material parameter across the likely ranges for the pieces of applicable equipment and different material batches.

At block 926, a modified signal function S' may be formed such that:

$$S' = S + \Delta S \quad (14)$$

where each component of S' is the direct sum of the corresponding components of S and the step-wise iterations of $\Delta S$.

This modified signal function S' is the modified version of the simulated optical metrology signal, i.e., signal function S, which has been customized to the parameters corresponding to the particular piece of metrology hardware and material batches being used. At block 928, the library of simulated optical metrology signals is adjusted.

It should be recognized that numerous modifications can be made to the process depicted in flow chart described above. For example, higher order polynomials may be used depending on the application. Additionally, each block can include many processes not explicitly described. Further, metrology signals other than optical metrology signals can be used, such as electron metrology signals in SEM.

When performing the above exemplary methods of adjusting the library for different parameter variables, there may be a different level of accuracy for each wavelength. Therefore, it would be desirable to identify the accuracy at different wavelengths and according to each wavelength's accuracy assign a weighting or remove them completely from the reconstructed signals. The reconstructed signals may include noise at certain wavelengths or ranges of wavelengths within the overall range of wavelengths spanned by the device. Thus, in one exemplary embodiment, specific wavelengths can be selected by determining one or more termination criteria, setting one or more selection criteria, and selecting wavelengths based on the selection criteria. One or more iterations of the selection step can be performed until the termination criteria are met. An exemplary method of selecting wavelengths is described in co-pending U.S. patent application Ser. No. 10/162,516 entitled "Selection of Wavelengths for Integrated Circuit Optical Metrology" filed on Jun. 3, 2002, which is incorporated in its entirety herein by reference.

Figure 11:
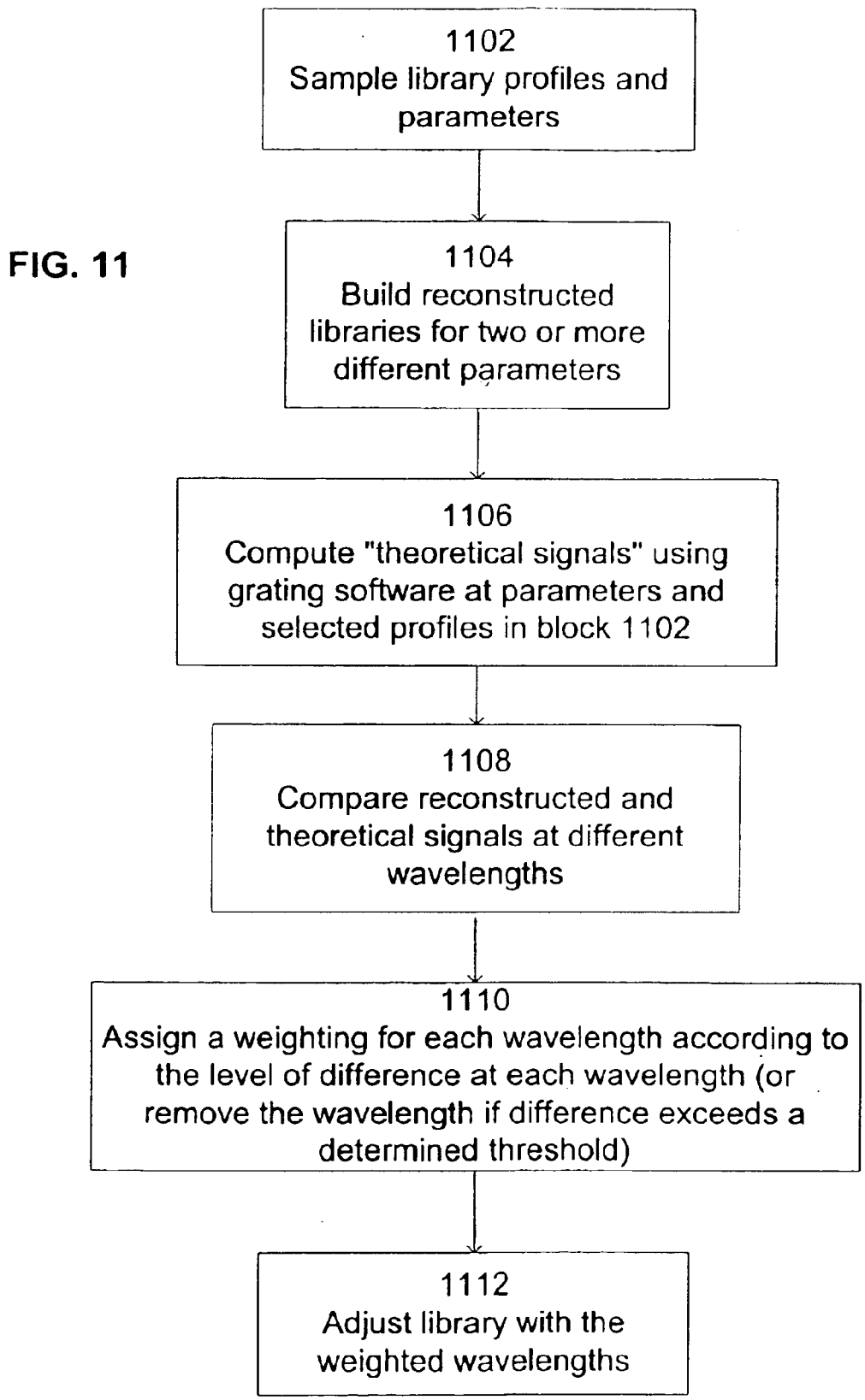
FIG. 11 is a flow chart of an exemplary process for weighting or removing wavelengths that introduce large inaccuracies in the adjusted libraries.

FIG. 11 is a flow chart of an exemplary process for weighting or removing wavelengths that introduce large inaccuracies in the reconstructed or adjusted libraries. At block 1102, several library profiles are sampled for different parameters. For example, several different angles of incidence can be used. Reconstructed or adjusted libraries are then built at block 1104 at some of the angles of incidence from block 1102. Simulated diffraction signals are then calculated at block 1106 using the angles and profiles used at block 1104. This can be done as if building a library based on the exact grating software, but limited to the few angles and profiles of block 1104.

At block 1108, the reconstructed and "theoretical signals" (simulated diffraction signals) are then compared with each other at different wavelengths. At block 1110, a difference is determined between each wavelength, and the difference can be related to a weighting for that particular wavelength. Additionally, a threshold value can be defined that if exceeded, will remove the wavelength. The weighting can also account for other factors such as the amount of information carried at each wavelength, for example with sensitivity analysis.

For example, a simple weighting factor could be:

$$1 - \Delta S / \Delta S_{average} \quad (15)$$

where $\Delta S$ is the change in a particular reconstructed signal with a corresponding simulated signal, for example, from block 1108, and $\Delta S_{average}$ is the average difference in reconstructed signals with simulated signals. Additionally, an exemplary threshold value could be a sum-squared-error (SSE) of 2.3, where a wavelength is excluded if the SSE is greater than or equal to 2.3.

Another exemplary scheme includes calculating a first $\Delta S$ from block 1108 and to create a first set of weighting factors.

Calculate a second ΔS as a difference between a measured signal S and a simulated signal S for the same wavelength for a given profile. Save the second ΔS as a second set of weighting factors. The first and second set of weighting factors can then be multiplied by each other to create a third set of weighting factors. The third set of weighting factors can then be compared to a threshold value, and if the threshold value is exceeded, the wavelengths can either be excluded or weighted based on the third set of weighting factors.

The reconstructed or adjusted library can then be used with the weighted wavelength information to obtain improved profile information at block 1112, for example, according to the exemplary techniques described above.

The above detailed description is provided to illustrate exemplary embodiments and is not intended to be limiting. It will be apparent to those skilled in the art that numerous modification and variations within the scope of the present invention are possible. Accordingly, the present invention is defined by the appended claims and should not be limited by the description herein.

We claim:

1. A method of generating sets of coefficients for use in optical metrology of semiconductor structures, comprising:
   obtaining at least three optical metrology signals for a set of parameters, wherein the optical metrology signals are indicative of light diffracted from a semiconductor structure, wherein a value of at least one parameter of the set of parameters is varied to produce each signal, and wherein the at least one parameter is varied over a nominal range that is less than or equal to a possible range of the set of parameters for an optical metrology system;
   obtaining functional relationships between the at least three optical metrology signals, wherein the functional relationships include at least three coefficient values; and
   determining at least three sets of coefficients from the at least three coefficient values of the obtained functional relationships.

2. The method of claim 1, wherein the at least three optical metrology signals were generated at a plurality of wavelengths.

3. The method of claim 1, wherein the at least three optical metrology signals were generated at a plurality of different angles of incidence.

4. The method of claim 1, wherein the functional relationships are determined at a plurality of measuring points.

5. The method of claim 1, wherein the sets of coefficients are stored and accessible by an optical metrology system.

6. The method of claim 1, wherein the functional relationships are polynomial functions.

7. The method of claim 1, wherein the sets of coefficients are used to create simulated optical metrology signals for different values of the at least one parameter.

8. The method of claim 1, wherein the sets of coefficients are used to create a library of simulated optical metrology signals for different values of the at least one parameter.

9. The method of claim 1, wherein the set of parameters includes:
   one or more hardware device parameters of an optical metrology system; and
   one or more material parameters of the semiconductor structure.

10. The method of claim 1, wherein the obtained optical metrology signals are diffraction spectra generated using Rigorous Coupled-Wave Analysis.

11. The method of claim 1, wherein the obtained optical metrology signals are diffraction spectra generated using a grating response simulator, and wherein the set of parameters are inputs to the grating response simulator.

12. The method of claim 1, wherein the at least three optical metrology signals are mathematical derivatives with respect to the at least one parameter.

13. The method of claim 1, wherein the determined sets of coefficients are used to adjust existing optical metrology signals.

14. The method of claim 13, wherein the existing optical metrology signals are part of an existing library.

15. A method of generating sets of coefficients for use in optical metrology of semiconductor structures, comprising:
   obtaining at least three optical metrology signals for a set of parameters, wherein the optical metrology signals are indicative of light diffracted from a semiconductor structure, and wherein a value of at least one parameter of the set of parameters is varied to produce each signal;
   obtaining functional relationships between the at least three optical metrology signals, wherein the functional relationships include at least three coefficient values, and wherein the functional relationships are a series of Fourier functions; and
   determining at least three sets of coefficients from the at least three coefficient values of the obtained functional relationships.

16. A method of generating sets of coefficients for use in optical metrology of semiconductor structures, comprising:
   obtaining at least three optical metrology signals for a set of parameters, wherein the optical metrology signals are indicative of light diffracted from a semiconductor structure and wherein a value of at least one parameter of the set of parameters is varied to produce each signal;
   obtaining functional relationships between the at least three optical metrology signals, wherein the functional relationships include at least three coefficient values and wherein the functional relationships are spline functions; and
   determining at least three sets of coefficients from the at least three coefficient values of the obtained functional relationships.

17. A method of generating sets of coefficients for use in optical metrology of semiconductor structures, comprising:
   obtaining at least three optical metrology signals for a set of parameters, wherein the optical metrology signals are indicative of light diffracted from a semiconductor structure, and wherein a value of at least one parameter of the set of parameters is varied to produce each signal;
   obtaining functional relationships between the at least three optical metrology signals, wherein the functional relationships include at least three coefficient values;
   determining at least three sets of coeffcents from the at least three coefficients are used to adjust a obtained functional relationships, wherein the determined sets of coefficients are used to adjust a simulated optical metrology signal generated using a set of parameters;
   obtaining one or more parameters associated with an optical metrology system,
     wherein the adjusted simulated optical metrology signal is to be used with the optical metrology system, and wherein the one or more parameters correspond to one or more parameters in the set of parameters used to generate the simulated optical metrology signal;

determining a difference between the one or more parameters associated with the optical metrology system and the corresponding one or more parameters in the set of parameters used to generate the simulated optical metrology signal;

dividing the determined difference into a number of intervals; and adjusting the simulated optical metrology signal step-wise over the number of intervals using the determined sets of coefficients.

18. The method of claim 17, wherein the number of intervals is greater than 40.

19. The method of claim 17, wherein the determined sets of coefficients are used to obtain partial derivative approximations.

20. The method of claim 19, wherein the obtained partial derivative approximations are used in a Jacobian matrix.

21. A method of generating optical metrology signals for use in optical metrology of semiconductor structures, comprising:

obtaining one or more parameters associated with an optical metrology system;

obtaining at least three optical metrology signals for a set of parameters, wherein the optical metrology signals are indicative of light diffracted from a semiconductor structure, wherein a value of at least one parameter of the set of parameters is varied to produce each signal, and wherein the at least one parameter is varied over a nominal range that is less than or equal to a possible range of the set of parameters for the optical metrology system;

obtaining functional relationships between the at least three optical metrology signals, wherein the functional relationships include at least three coefficient values;

determining at least three sets of coefficients from the at least three coefficient values of the obtained functional relationships; and determining optical metrology signals, which are to be used with the optical metrology system, using the at least three sets of coefficients and the one or more parameters associated with the optical metrology system.

22. The method of claim 21, wherein obtaining the one or more parameters associated with the optical metrology system includes:

obtaining one or more hardware device parameters of the optical metrology system.

23. The method of claim 21, wherein obtaining one or more parameters associated with the optical metrology system includes:

obtaining one or more material parameters of the semiconductor structures with which the optical metrology system will measure.

24. The method of claim 21, wherein the obtained and determined optical metrology signals are diffraction spectra generated using Rigorous Coupled-Wave Analysis.

25. The method of claim 21, wherein the obtained and determined optical metrology signals are diffraction spectra generated using a grating response simulator, and wherein the set of parameters are inputs to the grating response simulator.

26. The method of claim 21, wherein the functional relationships are polynomial functions.

27. The method of claim 21, wherein the functional relationships are determined at a plurality of measurement points.

28. The method of claim 27, where the measurement points include wavelength values.

29. The method of claim 27, where the measurement points include angle of incidence values.

30. The method of claim 21, wherein the sets of coefficients are stored and accessible by the optical metrology system.

31. A method of generating optical metrology signals for use in optical metrology of semiconductor structures, comprising:

obtaining one or more parameters associated with an optical metrology system;

obtaining at least three optical metrology signals for a set of parameters, wherein the optical metrology signals are indicative of light diffracted from a semiconductor structure, and wherein a value of at least one parameter of the set of parameters is varied to produce each signal;

obtaining functional relationships between the at least three optical metrology signals, wherein the functional relationships include at least three coefficient values, wherein the functional relationships are a series of Fourier functions;

determining at least three sets of coefficients form the at least three coefficient values of the obtained functional relationships: and determining optical metrology signals, which are to be used with the optical metrology system, using the at least three sets of coefficients and the one or more parameters associated with the optical metrology system.

32. A method of generating optical metrology signals for use in optical metrology of semiconductor structures, comprising:

obtaining one or more parameters associated with an optical metrology system;

obtaining at least three optical metrology signals for a set of parameters, wherein the optical metrology signals are indicative of light diffracted from a semiconductor structures, and wherein a value of at least one parameter of the set of parameters is varied to produce each signal;

obtaining functional relationships between the at least three optical metrology signals, wherein the functional relationships include at least three coefficient values, wherein the functional relationships are a spline functions;

determining at least three sets of coefficients form the at least three coefficient values of the obtained functional relationships; and determining optical metrology signals, which are to be used with the optical metrology system, using the at least three sets of coefficients and the one or more parameters associated with the optical metrology system.

33. A method of modifying a library of simulated optical metrology signals, comprising:

obtaining at least three simulated optical metrology signals, each simulated optical metrology signal generated using a set of parameters, each simulated optical metrology signal indicative of light diffracted from a semiconductor structure;

obtaining functional relationships between the at least three optical metrology signals, wherein the functional relationships include at least three coefficient values;

determining at least three sets of coefficients from the at least three coefficient values of the obtained functional relationships;

obtaining one or more parameters associated with an optical metrology system, the one or more parameters corresponding to one or more parameters in the sets of parameters used to generate the simulated optical metrology signals;

determining a difference between the one or more parameters associated with the optical metrology system and the corresponding one or more parameters in the sets of parameters used to generate the simulated optical metrology signals;

dividing the determined difference into a number of intervals; and adjusting a simulated optical metrology signal from the library step-wise over the number of intervals using the determined sets of coefficients.

34. The method of claim 33, wherein the number of intervals is greater than 40.

35. The method of claim 33, wherein adjusting a simulated optical metrology signal from the library includes using a Jacobian matrix.

36. The method of claim 35, further comprising:
determining a simulated optical metrology signal for a first parameter value based on:
a simulated optical metrology signal previously determined for a second parameter value preceding the first parameter value, the Jacobian matrix, and
an amount of change between the first and second parameter values.

37. The method of claim 36, further comprising:
calculating the Jacobian matrix using the sets of coefficients as partial derivative approximations.

38. The method of claim 33, further comprising:
forming a parameter modification vector having components equal to the variation between the at least one parameter value over each of the number of intervals;
forming the Jacobian matrix with elements corresponding to a change in the simulated optical metrology signal due to a change in a parameter value at a given wavelength; and
calculating a modification of the simulated optical metrology signal over each of the intervals based on the Jacobian matrix and the parameter modification vector.

39. A system of generating sets of coefficients for use in optical metrology of semiconductor structures, comprising:
a source configured to direct an optical metrology beam at a semiconductor structure;
a detector configured to measure the optical metrology beam diffracted from the semiconductor structure; and
a metrology profiler system configured to:
obtain at least three simulated optical metrology signals for a set of parameters, wherein the simulated optical metrology signals are indicative of light diffracted from a semiconductor structure, wherein a value of at least one parameter of the set of parameters is varied to produce each signal, and wherein the at least one parameter is varied over a nominal range that is less than or equal to a possible range of the set of parameters for an optical metrology system;
obtain functional relationships between the at least three simulated optical metrology signals, wherein the functional relationships include at least three coefficient values, and
determine at least three sets of coefficients from the at least three coefficient values of the obtained functional relationships.

40. The system of claim 39, wherein the determined sets of coefficients are used to modify a library of simulated optical metrology signals.

41. The system of claim 40, wherein the detector is configured to generate a measured optical metrology signal based on the measured optical metrology beam, and wherein the metrology profiler system is configured to compare the measured optical metrology signal to the modified library of simulated optical metrology signals.

42. The system of claim 39, wherein the sets of coefficients are used to adjust a simulated optical metrology signal.

43. The system of claim 42, wherein the detector is configured to generate a measured optical metrology signal based on the measured optical metrology beam, and wherein the metrology profiler system is configured to compare the measured optical metrology signal to the adjusted simulated optical metrology signals.

44. A computer-readable storage medium containing computer executable code to modify a library of metrology signals for varying parameters by instructing a computer to operate as follows:
obtaining at least three optical metrology signals for a set of parameters, wherein the optical metrology signals are indicative of light diffracted from a semiconductor structure, wherein a value of at least one parameter of the set of parameters is varied to produce each signal, and wherein the at least one parameter is varied over a nominal range that is less than or equal to a possible range of the set of parameters for an optical metrology system;
obtaining functional relationships between the at least three optical metrology signals, wherein the functional relationships include at least three coefficient values; and
determining at least three sets of coefficients from the at least three coefficient values of the obtained functional relationships.

45. The computer-readable storage medium of claim 44, wherein the at least three optical metrology signals were generated at a plurality of wavelengths.

46. The computer-readable storage medium of claim 44, wherein the at least three optical metrology signals were generated at a plurality of different angles of incidence.

47. The computer-readable storage medium of claim 44, wherein the functional relationships are determined at a plurality of measuring points.

48. The computer-readable storage medium of claim 44, wherein the sets of coefficients are stored and accessible by an optical metrology system.

49. The computer-readable storage medium of claim 44, wherein the functional relationships are polynomial functions.

50. The computer-readable storage medium of claim 44, wherein the sets of coefficients are used to create optical metrology signals for a different value of the at least one parameter.

51. The computer-readable storage medium of claim 44, wherein the sets of coefficients are used to create a library of optical metrology signals for a different value of the at least one parameter.

52. The computer-readable storage medium of claim 44, wherein the set of parameters includes:

one or more hardware device parameters of an optical metrology system; and one or more material parameters of the semiconductor structure.

53. The computer-readable storage medium of claim 44, wherein the obtained optical metrology signals are diffraction spectra generated using Rigorous Coupled-Wave Analysis.

54. The computer-readable storage medium of claim 44, wherein the obtained optical metrology signals are diffraction spectra generated using a grating response simulator, and wherein the set of parameters are inputs to the grating response simulator.

55. The computer-readable storage medium of claim 44, wherein the at least three signals are mathematical derivatives with respect to the at least one parameter.

56. The computer-readable storage medium of claim 44, wherein the determined sets of coefficients are used to modify existing optical metrology signals.

57. The computer-readable storage medium of claim 56, wherein the existing signals are part of an existing library.

58. The computer-readable storage medium of claim 44, wherein the sets of coefficients are used to adjust a simulated optical metrology signal generated using a set of parameters.

59. A computer-readable storage medium containing computer executable code to modify a library of metrology signals for varying parameters by instructing a computer to operate as follows:

obtaining at least three optical metrology signals for a set of parameters, wherein the optical metrology signals are indicative of light diffracted from a semiconductor structure and wherein a value of at least one parameter of the set of parameters is varied to produce each signal;

obtaining functional relationships between the at least three optical metrology signals, wherein the functional relationships include at least three coeffient value; and determining at least three sets of coefficients form the at least three coefficient values of the obtained functional relationships.

60. A computer-readable storage medium containing computer executable code to modify a library of metrology signals for varying parameters by instructing a computer to operate as follows:

obtaining at least three optical metrology signals for a set of parameters, wherein the optical metrology signals are indicative of light diffracted form a semiconductor structure, and wherein a value of at least one parameter of the set of parameters is varied to produce each signal;

obtaining functional relationships between the at least three optical metrology signals, wherein the functional relationships include at least three coefficient values, and wherein the functional relationships are spline functions; and determining at least three sets of coefficients form the at least three coefficient values of the obtained functional relationships.

61. A system of generating sets of coefficients for use in optical metrology of semiconductor structures, comprising:

a source configured to direct an optical metrology beam at a semiconductor structure;

a detector configured to measure the optical metrology beam diffracted from the semiconductor structure; and a metrology profiler system configured to:

obtain at least three simulated optical metrology signals for a set of parameters, wherein the simulated optical metrology signals are indicative of light diffracted from a semiconductor structure, and wherein a value of at least one parameter of the set of parameters is varied to produce each signal;

obtain functional relationships between the at least three simulated optical metrology signals, wherein the functional relationships include at least three coefficient values, and determine at least three sets of coefficients from the at least three coefficient values of the obtained functional relationships, wherein the determined sets of coefficients are used to modify a library of simulated optical metrology signals, and wherein the detector is configured to generate a measured optical metrology signal based on the measured optical metrology beam, andwherein the metrology library of simulated optical metrology signals.

62. A system of generating sets of coefficients for use in optical metrology of semiconductor structures, comprising:

a source configured to direct an optical metrology beam at a semiconductor structure;

a detector configured to measure the optical metrology beam diffracted from the semiconductor structure; and a metrology profiler system configured to:

obtain at least three simulated optical metrology signals for a set of parameters, wherein the simulated optical metrology signals are indicative of light diffracted from a semiconductor structure, and wherein a value of at least one parameter of the set of parameters is varied to produce each signal;

obtain functional relationships between the at least three simulated optical metrology signals, wherein the functional relationships include at least three coefficient values, and determine at least three sets of coefficients from the at least three coefficient values of the obtained functional relationships, wherein the sets of coefficients are used to adjust a simulated optical metrology signal, and wherein the detector is configured to generate a measured optical metrology signal based on the measured optical metrology beam, and wherein the metrology profiler system is configured to compare the measured optical metrology signal to the adjusted simulated optical metrology signals.

* * * * *